United States Patent [19]
Puckette

[11] Patent Number: 5,498,584
[45] Date of Patent: Mar. 12, 1996

[54] PROCESS FOR THE SELECTIVE HYDROGENATION OF EPOXYALKENES TO EPOXYALKANES

[75] Inventor: Thomas A. Puckette, Longview, Tex.

[73] Assignee: Eastman Chemical Company, Kingsport, Tenn.

[21] Appl. No.: 311,628

[22] Filed: Sep. 23, 1994

Related U.S. Application Data

[62] Division of Ser. No. 262,122, Jun. 17, 1994.

[51] Int. Cl.$^6$ ...................................................... B01J 31/00
[52] U.S. Cl. ........................... 502/162; 502/166; 585/277; 585/275
[58] Field of Search ...................... 502/162, 166; 585/277, 275

[56] References Cited

U.S. PATENT DOCUMENTS

| | | | |
|---|---|---|---|
| 4,743,699 | 5/1988 | Page et al. | 556/23 |
| 4,863,639 | 9/1989 | Heggie et al. | 260/351.5 |
| 4,999,443 | 3/1991 | Bertleff et al. | 556/136 |
| 5,334,791 | 8/1994 | Cavell et al. | 502/166 |

OTHER PUBLICATIONS

Schrock, R. R. et al, J.A.C.S. 93:10, pp. 2397–2407, 1971 (I).
Schrock, R. R. et al., J.A.C.S. 98:8, pp. 2143–2147, 1976 (II).
Fujitsu, H., et al., J.A.C.S., Perkin I, 855–859, 1982.
Crabtree, R. H., et al., J. Organometallic Chemistry, 141, pp. 113–121, 1977.
Landis, C. R., et al., J. Organometallic Chemistry, 250 pp. 485–490, 1983.

Primary Examiner—Sharon Gibson
Attorney, Agent, or Firm—J. Frederick Thomsen; Harry J. Gwinnell

[57] ABSTRACT

Disclosed in a process for the homogeneous, catalytic hydrogenation of epoxyalkenes and epoxycyclo-alkenes, especially conjugated γ,δ-epoxyalkenes and epoxycycloalkenes, to the corresponding epoxyalkanes and epoxycycloalkanes using a solution of a complex rhodium catalyst whereby the olefinic unsaturation is hydrogenated without significant hydrogenolysis of the conjugated epoxy group.

7 Claims, No Drawings

PROCESS FOR THE SELECTIVE HYDROGENATION OF EPOXYALKENES TO EPOXYALKANES

This is a divisional application of copending application Ser. No. 08/262,122 filed Jun. 17, 1994.

This invention pertains to a novel process for the conversion of epoxyalkenes and epoxycycloalkenes, especially conjugated γ,δ-epoxyalkenes and γ,δ-epoxy-cycloalkenes to the corresponding epoxyalkanes and epoxycycloalkanes. More specifically, this invention pertains to the homogeneous, catalytic hydrogenation of epoxyalkenes and epoxycycloalkenes in a solution of a complex rhodium catalyst whereby the olefinic unsaturation is hydrogenated without significant hydrogenolysis of the conjugated epoxy group.

The selective hydrogenation of unsaturated epoxides has been reported previously under a variety of heterogeneous and homogenous conditions. The heterogeneous process are easily differentiated from the present invention by the heterogeneous nature of the catalyst but are included here to give more a complete understanding of the prior art.

U.S. Pat. No. 5,077,418 discloses a heterogeneous process for converting unsaturated epoxides into the corresponding saturated epoxides utilizing a supported rhodium catalyst. The process is carried out in the temperature range of 25° to 80° C. under an atmosphere of hydrogen at 2 to 56 bar (29 to 812 psia). Hydrogenation of 3,4-epoxy-1-butene with this process produces a mixture of butylene oxide, butyraldehyde, and butanol. The butyraldehyde is subsequently hydrogenated over nickel catalyst to convert it to butyl alcohol which is readily separated from butylene oxide.

Chernyshkova et al (Neftekhimiya 14, 677–681 (1974), Chem. Abs. 82:72667p) have reported a similar reaction utilizing supported rhodium, palladium, and platinum catalysts in the hydrogenation of epoxycyclododecadienes to epoxycyclododecane. These workers used alumina-supported rhodium catalysts at 75° to 100° C. to achieve a 92 to 96% yield of the desired epoxide.

Chernyshkova (SU 380,650) also has reported the hydrogenation of epoxycyclododecadienes to epoxycyclododecane using the same process as is described in the Neftekhimiya article and specifying further the use of alumina and carbon supported catalysts. The experimental conditions reported include the operation of the process at 150° to 165° C. and 100 atmospheres of hydrogen with a ruthenium on alumina catalyst. These conditions gave complete reaction in 70 minutes and a product mixture which was greater than 85% epoxycyclododecane. Other products reported include the cyclic ketone, alcohol, and a small amount of the cyclic hydrocarbon. Japanese Patent 74-41,193 discloses the same reaction as Chernyshkova et al but utilizes a palladium on carbon catalyst in the presence of an additive which may be a neutral salt such as an alkali metal halide or a base such as alkali hydroxides and amines.

Anderson et al (U.S. Pat. No. 4,127,594) report the selective hydrogenation of unsaturations in the presence of epichlorohydrin. The primary targets in this reaction are chloroacroleins and 5,6-epoxy-1-hexene which are formed as impurities in the epichlorohydrin manufacturing process. The process converts the unsaturated epoxy hexene to the saturated epoxide which does not interfere with downstream uses of epichlorohydrin. The process of the '594 patent typically operates at 100 psig and 50° to 80° C. and achieves complete conversion of the unsaturated epoxide to the saturated product. The catalysts used in the process are rhodium, platinum and palladium supported on non-acidic, refractory supports such as alpha-alumina.

Balbolov et al, have reported in the *Journal of Molecular Catalysts* 69, 95–103 (1991) a study on the kinetics of the hydrogenation of 1,2-epoxycyclododeca-5,9-diene to epoxy cyclododecane using supported palladium catalysts wherein the support materials were alumina, titanium dioxide, and carbon. Titanium dioxide-supported catalysts gave the least desirable results while carbon-supported catalysts gave the best reported results of 90.9% selectivity for the saturated epoxide at 100° C. and 1.3 MPa (12.8 atmospheres) pressure of hydrogen.

The prior art which describes the homogenous, catalytic hydrogenation of unsaturated epoxides is limited to two reports by Mochida, Fujitsu and co-workers. Mochida (Chemical Letters, 10, 1025–1026 (1975)) has reported a study on the use of Wilkinson's catalyst [tris(triphenylphosphine)rhodium chloride] for the hydrogenation of 3,4-epoxy-1-butene and other small ring compounds such as cyclopropanes. Mochida found that epoxybutene reacts slowly under mild conditions to give a mixture of products which are primarily derived from ring opening reactions. A mechanistic pathway is proposed which involves crotyl alcohol and crotonaldehyde as intermediates. Under the conditions used by Mochida (30° C., 10 hours), Wilkinson's catalyst gave a 60% conversion of epoxy butene to a mixture of products which was composed of butylene oxide (40%), butyraldehyde (48 %) and butanol (12%).

Fujitsu, Mochida, and co-workers (*J. Chem. Soc. Perkin I*, 855 (1982)) have reported a study utilizing cationic rhodium catalysts for the homogenous hydrogenation of 3,4-epoxy-1-butene. This group used the preparative methods of Schrock and Osborn (*J. Am. Chem. Soc.*, 93, 2397 (1971)). Fujitsu reports modifications to the Schrock and Osborn catalysts by substituting other phosphine ligands such as triethylphosphine, trimethylphosphine and 1,2-bis-(diphenylphos-phino)ethane for the ligands of the Schrock procedure. The Fujitsu work was conducted primarily at one atmosphere of hydrogen and 30° C. although Fujitsu does report one run at 50 atmospheres (735 psig). The products obtained by Fujitsu at one atmosphere and 30° C. are primarily derived from ring opening reactions. The product yields are phosphine ligand dependent and vary greatly. For example, after 8 hours of reaction with triethylphosphine as the ligand, the products include crotonaldehyde (34.9%), butyraldehyde (15.1%), 3-butene-1-ol (10.8%), 2-butene-1-ol (20.7%), and butylene oxide (8.9%). The previous use of Wilkinson's catalyst by Mochida (discussed above) for this reaction is given again as an example in the Fujitsu paper. As previously reported in the Mochida paper, Wilkinson's catalyst at long reaction times (10 hours) and mild conditions (1 atmosphere hydrogen pressure, 30° C.) produces the saturated epoxide in 40% yield in addition to butyraldehyde (48%) and butanol (12%). The highest reported yield of butylene oxide in the Fujitsu paper is the single run at 50 atmospheres of hydrogen. A 41.8% conversion of the epoxybutene was observed after one hour of reaction. The products observed were butylene oxide (12.6%), 3-butene-1-ol (10.6%), crotonaldehyde (7.8%), and 2-butene-1-ol (6.4%), butanol (3%), and butyraldehyde (1.4%). Again, the primary reaction pathway is by cleavage of the epoxide ring.

The present invention provides an improvement over the existing methods for the hydrogenation of unsaturated epoxides to the corresponding saturated epoxides, especially those in which the carbon-carbon double bonds are in conjugation with the epoxide functional group. More specifically, the process of this invention hydrogenates 3,4-epoxy-1-butene to 1,2-butylene oxide in high yield with good selectivity and at commercially-acceptable reaction rates. One embodiment of the invention is a process for the preparation of epoxyalkanes and epoxycycloalkanes by hydrogenating under hydrogenation conditions of temperature and pressure γ,δ-epoxyalkenes and γ,δ-epoxycycloalkenes in a catalyst solution comprising (A) an inert, organic solvent and (B) catalyst components dissolved in said solvent comprising (i) rhodium, (ii) an organophosphorus compound selected from trihydrocarbylphosphines and trihydrocarbylphosphites, and (iii) a poly-unsaturated hydrocarbon selected from alkadienes, cycloalkadienes, alkatrienes and cycloalkatrienes;

wherein the ratio of component (ii) to rhodium gives a gram atoms of phosphorus per gram atom of rhodium ratio of greater than 3:1 up to about 50:1 and the ratio of moles of component (iii) to gram atoms of rhodium is about 2:1 to 150:1.

A second embodiment of my invention comprises the catalyst solution defined above.

The epoxyalkene and epoxycycloalkene reactants may contain from 4 to about 20 carbon atoms, preferably from 4 to about 8 carbon atoms. The present invention is especially useful in achieving the selective hydrogenation of conjugated γ,δ-epoxyalkene and γ,δ-epoxycycloalkene to obtain the corresponding epoxyalkane and epoxycycloalkane. Examples of the γ,δ-epoxyalkene and γ,δ-epoxycycloalkene reactants include compounds having the structural formula:

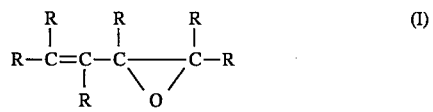
(I)

wherein each R is independently selected from hydrogen, alkyl of up to about 8 carbon atoms, a carbocyclic or heterocyclic aryl group of about 5 to 10 carbon atoms or halogen or any two R substituents collectively may represent an alkylene group forming a ring, e.g., alkylene containing in the main chain 4 to about 6 carbon atoms. The preferred epoxyalkene reactants comprise compounds of formula (I) wherein the R substituents individually represent hydrogen, lower alkyl, e.g., alkyl of up to about 4 carbon atoms, or halogen or collectively represent straight or branched chain alkylene of 4 to about 8 carbon atoms, especially compounds of formula (I) wherein at least 4 of the R groups represent hydrogen. Exemplary compounds contemplated for use in the practice of the present invention include 3,4-epoxy-3-methyl-1-butene, 2,3-dimethyl-3,4-epoxy-1-butene, 1,3-cyclooctadiene monoepoxide, 3,4-epoxy-1-butene, and the like. The epoxyalkene reactant of primary interest is 3,4-epoxy-1-butene.

The epoxyalkane and epoxycycloalkane compounds produced in accordance with the present invention have the formula

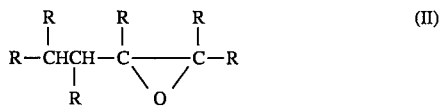
(II)

wherein the R substituents are defined above. These compounds are useful in the manufacture of polyethers, alkylene and cycloalkylene glycols, aminoalkanols and aminocycloalkanols, epoxy resins, urethane polyols, nonionic surfactants and stabilizers for chlorinated hydrocarbons.

The rhodium component of the catalyst solution can be provided by any one of various rhodium compounds soluble in the inert, organic solvent in which the catalyst solution is formulated and in which the hydrogenation is carried out. Examples of such soluble rhodium compounds include tris(triphenylphosphine)-rhodium chloride, tris(triphenylphosphine)rhodium bromide, tris(triphenylphosphine)rhodium iodide, rhodium 2-ethylhexanoate dimer, rhodium acetate dimer, rhodium butyrate dimer, rhodium valerate dimers, rhodium carbonate, rhodium octanoate dimer, dodecacarbonyltetrarhodium, rhodium(III) 2,4-pentanedionate, rhodium(I) dicarbonyl acetonylacetonate, tris(triphenylphosphine)-rhodium carbonyl hydride [(Ph3P:)3Rh(CO)-H], and cationic rhodium complexes such as rhodium(cycloocta-diene)bis(tribenzylphosphine) tetraflouroborate and rhodium (norbornadiene)bis(triphenylphosphine) hexaflourophosphate.

The activity and selectivity of the catalyst solution has been found to be relatively insensitive to the source of the rhodium. The concentration of rhodium [Rh] in the catalyst solution may be in the range of about 20 to 20,000 ppm although very low concentrations of rhodium are not commercially desirable since reaction rates will be unacceptably low. The upper limit on the rhodium concentration is not critical and is dictated principally by the high cost of rhodium. Thus, the concentration of rhodium [Rh] in the catalyst solution preferably is in the range of 100 to 2000 and, most preferably, 200 to 1000 ppm.

Examples of some of the tertiary (trisubstituted) phosphine and phosphite compounds which may be employed as the organophosphorus component of the novel catalyst solution provided by the present invention include tri-butylphosphine, tributylphosphite, butyldiphenylphosphine, dibutylphenylphosphite, tribenzylphosphine, tribenzylphosphite, tricyclohexylphosphine, tricyclohexylphosphite, 1,2-bis(diphenylphosphino)ethane, 1,3-bis(di-phenylphosphino)propane, 1,4-butanebis(dibenzylphosphite), 2,2'-bis(diphenylphosphinomethyl)-1,1'-biphenyl, and 1,2-bis(diphenylphosphinomethyl)benzene. Additional examples of tertiary phosphines are disclosed in U.S. Pat. Nos. 4,845,306, 4,742,178, 4,774,362, 4,871,878 and 4,960,949. Typical phosphine and phosphite ligands may be represented by the general formulas

(III)

and

(IV)

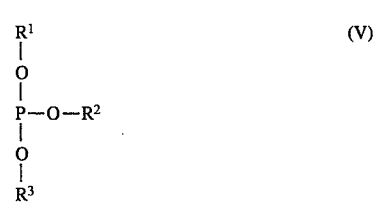
(V)

and

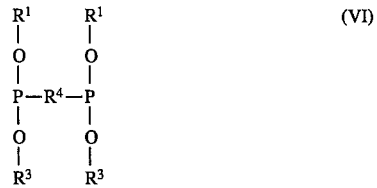
(VI)

wherein $R^1$, $R^2$ and $R^3$ are the same or different and each is hydrocarbyl containing up to about 12 carbon atoms and $R^4$ is a hydrocarbylene group which links the 2 phosphorus atoms through a chain of 2 to 8 carbon atoms. Examples of the hydrocarbyl groups which $R^1$, $R^2$ and $R^3$ may represent include alkyl including aryl-substituted alkyl such as benzyl, cycloalkyl such as cyclohexyl, and aryl such as phenyl and phenyl substituted with one or more alkyl groups. Alkylene such as ethylene, trimethylene and hexamethylene, cycloalkylene such as cyclohexylene, and phenylene, naphthylene and biphenylene are examples of the hydrocarbylene groups which $R^4$ may represent.

The organophosphorus component of the catalyst solution preferably is a trisubstituted mono-phosphine compound such as those having formula (I) above. Triphenylphosphine, tricyclohexylphosphine and, especially, tribenzylphosphine are the most preferred organophosphorus compounds. The ratio of moles of organophosphorus compound to gram atoms of rhodium present in the catalyst system preferably is about 4:1 to 20:1.

The poly-unsaturated hydrocarbon component of the novel catalyst solution employed in the present invention may be either cyclic or acyclic and may contain other functional groups. Examples of suitable dienes are 1,5-cyclooctadiene, 1,3-cyclooctadiene, butadiene, 1,3-pentadiene, norbornadiene, 1,5-hexadiene, dicyclopentadiene and 1,7-octadiene. Examples of possible trienes include 1,5,9-cyclododecatriene and 1,5,7-octatriene. The poly-unsaturated hydrocarbon may contain up to about 12 carbon atoms. Dienes having about 4 to 10 carbon atoms and having a boiling point in the range of about −5° to 240° C. are preferred. The ratio of moles of the poly-unsaturated hydrocarbon catalyst component per gram atom of rhodium preferably is in the range of about 5 to 10.

The inert, organic solvent which contains the active components of the novel catalyst solution may be selected from a wide variety of compounds such as ketones; aldehydes; esters; alcohols; aliphatic, cycloaliphatic and aromatic hydrocarbons; aromatic halides; aliphatic and cyclic ethers; N,N-dialkylamides of lower carboxylic acids; acetals; ketals; and similar non-reactive, liquid, organic materials. Generally, the inert, organic solvent may contain up to about 12 carbon atoms. The epoxyalkane or epoxycycloalkane product also can serve as the solvent for the process. Examples of typical ester solvents include $C_1$ to $C_6$ alkyl esters of aliphatic, cycloaliphatic and aromatic carboxylic acids, including dicarboxylic acids, containing up to about 6 carbon atoms. The inert solvent preferably is selected from aliphatic and cycloaliphatic ketones containing 3 to 8 carbon atoms such as acetone, 2-butanone, 2-hexanone and cyclohexanone. The inert, organic solvent may contain water, e.g., up to about 15 weight percent water (based on the weight of the organic solvent), to aid in dissolving optional. inorganic materials described below. Normally, the solvent will not contain more than about 5 weight percent water (same basis).

The hydrogenation conditions of pressure and temperature may be varied considerably, e.g., total pressures of about 1 to 100 bars (absolute) and temperatures of about 25° to 100° C. However, the preferred conditions comprise total pressures in the range of 25 to 80 bars (absolute) and temperatures in the range of 40° to 70° C.

The reactivity and selectivity of the abovedescribed catalyst solution is enhanced by the inclusion therein of a non-nucleophilic (gegen) anion such as tetraphenylboron, tetraflouroborate, hexaflourophosphate, and tetrapyrazolylborates, e.g., tris(3,5-di-methyl- 1-pyrazolyl)borohydride. The boron-containing gegen anion may be selected from compounds having the general formula $(R^5)_4B^- M^+$ wherein $R^5$ is selected from fluorine, hydrogen, alkyl, aryl, e.g., unsubstituted and substituted phenyl and naphthyl, or hetero aryl in which at least one of the ring hetero atoms is nitrogen, e.g., pyrazolyl residues, and M is an alkali metal such as potassium, sodium, lithium, etc. It is apparent that those skilled in the art will recognize from the literature, e.g., Schrock and Osborn, *J. Am. Chem. Soc.*, 93, 2397, 3089 (1971) and ibid, 98, 2134, 4450 (1976), that various anionic materials may be employed to provide a gegen ion which will have a favorable effect upon the process of the present invention. The non-nucleophilic gegen ion may be provided as an inorganic salt such as an alkali metal salt or as an organic onium salt such as the salt of quaternary ammonium or phosphonium cation, e.g., tetrahydrocarbyl ammonium and phosphonium cations having a total carbon content of up to about 32 carbon atoms. Examples of such hydrocarbyl groups are set forth in the above definitions of $R^1$, $R^2$ and $R^3$. If the gegen ion source compound is readily soluble in the solvent, a small amount of water can be added the solvent to increase the gegen ion solubility. The amount of the non-nucleo-philic gegen ion employed usually will be at least 2, and preferably about 5 to 15, moles per gram atom of rhodium present.

The selectivity of the catalyst system can be further enhanced in many cases by the presence of added halide, especially added iodide, to the catalyst solution. The iodide ion may be provided in the form of iodide salts such as alkali metals iodides, e.g., potassium, sodium and lithium iodide. The amount of iodide which will produce a beneficial effect is 0.1 gram atoms or more iodide per gram atom rhodium present. Preferred levels of iodide ion are in the range of about 0.25 to 5.0 gram atoms iodide per gram atom rhodium.

The hydrogenation process of the present invention may be carried out in a batch, semi-continuous or continuous mode of operation. For example, in batch operation the unsaturated epoxide and the catalyst solution are charged to an autoclave at atmospheric pressure and ambient temperature under a protective nitrogen atmosphere. The mixture is then charged to the desired pressure, usually 42 to 70 bars absolute, stirred and heated to the desired reaction temperature, typically 60° C. After the desired reaction time has elapsed, usually 1 hour, the autoclave and contents are cooled and the excess hydrogen is vented. The hydrogenated epoxide product may be recovered by conventional separation techniques, e.g., distillation, selective crystallization or extraction, depending on various factors such as the particular epoxide produced, the solvent and catalyst components used, and other process variables.

In continuous operation of the process, the unsaturated epoxide reactant and catalyst are fed continuously to a heated reaction zone, e.g., an agitated pressure vessel or series of agitated pressure vessels, under a hydrogen or hydrogen-containing atmosphere at elevated pressure. The hydrogen used in the process may be essentially pure hydrogen or hydrogen containing minor amounts of one or more inert impurities generated in hydrogen plants may be used. Examples of such inert impurities or components include nitrogen, argon or methane. The residence time within the reaction zone is sufficient to allow for the conversion of the reactant to the desired product. A product stream is withdrawn continuously from the reaction zone and fed to a product recovery zone. Product recovery may utilize various conventional methods. For example, if the product is sufficiently volatile, the product may be recovered by vapor stripping the product out of the catalyst solution using an inert gas such as nitrogen or hydrogen. If the product is not sufficiently volatile to permit vapor stripping, the product may be recovered by conventional distillation techniques. If the epoxide product is highly functionalized or contains highly polar substituents, the product may be recovered by extraction techniques. If the epoxide product is crystalline, it may be isolated by selective crystallization of the product from the catalyst solution.

The hydrogenation process and catalyst provided by the present invention are further illustrated by the following examples. All catalyst solutions were prepared under a nitrogen atmosphere unless stated otherwise. All of the poly-unsaturated hydrocarbons and solvents used were filtered through silica gel to remove peroxide impurities and were stored under nitrogen prior to use. All autoclaves were nitrogen purged prior to charging the catalyst to the autoclave.

The reactants and products were analyzed by gas chromatography on a Hewlett Packard Model 5890 Gas Chromatograph equipped with a thermal conductivity detector. The chromatograph was equipped with a J&W Scientific DB Wax capillary column (Part # 123-7033, 30 meter×0.32 mm ID with 0.5 micron film) using a 0.5 microliter (µL) sample. Helium was used as the carrier gas (30 kPa head pressure) and the oven temperature profile for the run was 45° C. initial temperature (5 minute hold), then programmed heating at 15° C. per minute to 220° C. (19 minute hold).

EXAMPLE 1

A mixture of tris(triphenylphosphine)rhodium chloride (0.1 g), tribenzylphosphine (0.1 g), 1,5-cyclo-octadiene (0.1 mL) and 50 mL of 2-heptanone in a 250 mL flask equipped with a stirring bar was stirred under hydrogen at ambient temperature and atmospheric pressure until all of the solids were dissolved to produce a light yellow catalyst solution. 3,4-Epoxy- 1,2-butene (10 mL) was added to the catalyst solution and the resulting solution was fed under nitrogen via tubing to a 300 mL autoclave which had been purged with nitrogen. The stirrer was started and then the autoclave was pressurized to 70 bars absolute (1000 pounds per square inch - psig) with hydrogen (no inerts were added) and the autoclave was heated to 60° C. over a period of 5–10 minutes. The reaction mixture was stirred and maintained at a temperature of 60° C. and a hydrogen pressure of about 56–70 bars absolute (800–1000 psig) for 1 hour. The autoclave then was cooled, depressurized and a sample of the product mixture was analyzed by the procedure described above.

The results obtained are shown in Table I wherein "EpB Conv" is moles of 3,4-epoxy-1-butene converted to other compounds divided by the moles of 3,4-epoxy-1butene employed in the experiment X 100, "BO %" is the moles of butylene oxide (1,2-epoxyubutane) produced divided by moles of 3,4-epoxy-1-butene converted to other compounds X 100, "HBu" is the moles of butyraldehyde produced divided by moles of 3,4-epoxy-1-butene converted to other compounds X 100, and "BuOH %" is the moles of butanol produced divided by moles of 3,4-epoxy-1-butene converted to other compounds X 100.

EXAMPLE 2

The procedure described in Example 1 was repeated except that (1) the rhodium source compound was (Ph$_3$P)$_3$Rh(CO)H wherein Ph is phenyl (0.108 mol) and (2) tetraphenylboron sodium (0.06 g) was included in the catalyst solution. The results are shown in Table I.

EXAMPLE 3

The procedure described in Example 1 was repeated except that (1) the rhodium source compound was Rh(CO)$_2$CH$_3$COCHCOCH$_3$ (0.108 mol) and (2) tetraphenylboron sodium (0.06 g) was included in the catalyst solution. The results are shown in Table I.

EXAMPLE 4

The procedure described in Example 1 was repeated except that (1) the rhodium source compound was tris(triphenylphosphino)rhodium bromide (0.108 mol) and (2) tetraphenylboron sodium (0.06 g) was included in the catalyst solution. The results are shown in Table I.

EXAMPLE 5

The procedure described in Example 1 was repeated except that (1) the rhodium source compound was tris(triphenylphosphino)rhodium iodide (0.108 mol) and (2) tetraphenylboron sodium (0.06 g) was included in the catalyst solution. The results are shown in Table I.

EXAMPLE 6

The procedure described in Example 1 was repeated except that tetraphenylboron sodium (0.06 g) was included in the catalyst solution. The results are shown in Table I.

EXAMPLE 7

The procedure described in Example 1 was repeated except that the rhodium source compound was rhodium (1,5-cyclooctadiene)bis(tribenzylphosphine) hexafluorophosphate (0.108 mol). The results are shown in Table I.

EXAMPLE 8

The procedure described in Example 1 was repeated except that the rhodium source compound was rhodium (1,5-cyclooctadiene)bis(tribenzylphosphine) tetraphenylboron (0.108 mol). The results are shown in Table I.

EXAMPLE 9

The procedure described in Example 1 was repeated except that (1) the rhodium source compound was rhodium 2-ethylhexanoate dimer (0.108 mol), (2) tetraphenylboron sodium (0.06 g) and (3) sodium iodide (0.05 g) were included in the catalyst solution. The results are shown in Table I.

EXAMPLE 10

The procedure described in Example 6 was repeated except that sodium iodide (0.05 g) was included in the catalyst solution. The results are shown in Table I.

EXAMPLE 11

The procedure described in Example 8 was repeated except that sodium iodide (0.05 g) was included in the catalyst solution. The results are shown in Table I.

EXAMPLE 12

The procedure described in Example 6 was repeated except that the poly-unsaturated hydrocarbon component of the catalyst was 1,3-cyclooctadiene (0.10 mL). The results obtained are shown in Table I.

EXAMPLE 13

The procedure described in Example 6 was repeated except that the poly-unsaturated hydrocarbon component of the catalyst was norbornadiene (0.10 mL). The results obtained are shown in Table I.

EXAMPLE 14

The procedure described in Example 6 was repeated except that the poly-unsaturated hydrocarbon component of the catalyst was 1,5,9-cyclododecatriene (0.10 mL). The results obtained are shown in Table I.

EXAMPLE 15

The procedure described in Example 6 was repeated except that the amount of 1,5-cyclooctadiene employed was (0.20 mL). The results obtained are shown in Table I.

EXAMPLE 16

The procedure described in Example 6 was repeated except that the amount of 1,5-cyclooctadiene employed was (0.30 mL). The results obtained are shown in Table I.

EXAMPLE 17

To a mixture of powdered potassium hexafluorophosphate (0.06 g, 0.33 millimoles - mmol) and water (1.0 mL) in a 3-neck, 250 mL flask equipped with a stirring bar was added, under nitrogen, tris(triphenylphosphine)-rhodium chloride (0.1 g), tribenzylphosphine (0.1 g), 1,5-cyclooctadiene (0.1 mL) and acetone (2.0 mL). The resulting catalyst combination was swirled to mix the components and then stirred under hydrogen for 5 minutes. 2-Heptanone (50 mL) then was added and stirring under hydrogen was continued until all of the solids are dissolved to provide a light yellow catalyst solution. 3,4-Epoxy-1,2-butene (10 mL) was added to the catalyst solution and the resulting solution was fed under nitrogen via tubing to a 300 mL autoclave which had been purged with nitrogen. The stirrer was started and then the autoclave was pressurized to 70 bars absolute (1000 psig) with hydrogen (no inerts were added) and the autoclave was heated to 60° C. over a period of 5–10 minutes. The reaction mixture was stirred and maintained at a temperature of 60° C. and a hydrogen pressure of about 56–70 bars absolute (800–1000 psig) for 1 hour. The autoclave then was cooled, depressurized and a sample of the product mixture was analyzed by the procedure described above. The results obtained are shown in Table I.

EXAMPLE 18

Example 17 was repeated except that the potassium hexafluorophosphate was replaced with sodium tetra-fluoroborate (0.018 mmol). The results obtained are shown in Table I.

EXAMPLE 19

Example 17 was repeated except that the potassium hexafluorophosphate was replaced with tetraphenylboron sodium (0.018 millimoles - mmol). The results obtained are shown in Table I.

EXAMPLE 20

Example 6 was repeated except that the tetraphenylboron sodium was replaced with potassium tris(3-methyl- 5-phenylpyrazolyl)hydridoborate (0.018 mmol). The results obtained are shown in Table I.

EXAMPLE 21

Example 6 was repeated except that the tetraphenylboron sodium was replaced with tetrabutylammonium p-tolylsulfonate (0.018 mmol). The results obtained are shown in Table I.

EXAMPLE 22

Example 13 was repeated except that the tetraphenylboron sodium was replaced with tetrabutylammonium hexafluorophosphate (0,018 mmol). The results obtained are shown in Table I.

EXAMPLE 23

Example 13 was repeated except that the tetra-phenylboron sodium was replaced with tetrabutylammonium hexafluoroborate (0,018 mmol). The results obtained are shown in Table I.

EXAMPLE 24

Example 1 was repeated except that (1) tetraphenyl-boron sodium (0.06 g) was included in the catalyst solution and (2) the reaction temperature was 40° C. The results obtained are shown in Table I.

EXAMPLE 25

Example 1 was repeated except that (1) tetrabutylammonium hexafluorophosphate (0.07 g) was included in the catalyst solution, (2) the poly-unsaturated hydrocarbon component of the catalyst was norbornadiene (0.1 mL), and (3) the reaction temperature was 50° C. The results obtained are shown in Table I.

EXAMPLE 26

The procedure of Example 1 was repeated except that (1) the organophosphorus compound was dioctylphenylphosphine (0.1 g), (2) tetraphenylboron sodium (0.06 g) was included in the catalyst solution, (3) the inert, organic solvent was acetone, and (4) the reaction period was 2 hours. The results obtained are shown in Table I.

EXAMPLE 27

The procedure of Example 1 was repeated except that (1) tetrabutylammonium hexafluorophosphate (0.07 g) was included in the catalyst solution and (2) the poly-unsaturated hydrocarbon component of the catalyst was norbornadiene (0.1 mL), The results obtained are shown in Table I.

EXAMPLE 28

Example 27 was repeated except that the hydrogenation was carried out at 70° C. The results obtained are shown in Table I.

EXAMPLE 29

Example 27 was repeated except that the hydrogenation was carried out at 80° C. The results obtained are shown in Table I.

EXAMPLE 30

Example 29 was repeated except that the organo-phosphorus compound was dioctylphenylphosphine (0.1 g). The results obtained are shown in Table I.

EXAMPLE 31

Example 6 was repeated except that the hydrogenation was carried out at a hydrogen pressure of 14.8 bars absolute (200 psig) o The results obtained are shown in Table I.

EXAMPLE 32

Example 6 was repeated except that the hydrogenation was carried out at a hydrogen pressure of 35.5 bars absolute (500 psig). The results obtained are shown in Table I.

EXAMPLE 33

Example 6 was repeated except that the hydrogenation was carried out at a hydrogen pressure of 104.4 bars absolute (1500 psig). The results obtained are shown in Table I.

EXAMPLE 34

Example 6 was repeated except that (1) the organophosphorus compound component of the catalyst system was dioctylphenylphosphine (0.1 g), (2) the process solvent was acetone (50 mL), and (3) the hydrogenation was carried out over a period of 2 hours. The results obtained are shown in Table I.

EXAMPLE 35

Example 6 was repeated except that (1) the organophosphorus compound component of the catalyst system was trioctylphosphine (0.1 g), (2) the process solvent was 2,2,4-trimethyl-1,3-pentanediol monoisobutyrate (50 mL), and (3) the hydrogenation was carried out over a period of 2 hours. The results obtained are shown in Table I.

EXAMPLE 36

Example 6 was repeated except that (1) the organophosphorus compound component of the catalyst system was tricyclohexylphosphine (0.3 g), (2) the process solvent was 2,2,4-trimethyl-1,3-pentanediol monoisobutyrate (50 mL), and (3) the hydrogenation was carried out over a period of 2 hours. The results obtained are shown in Table I.

EXAMPLE 37

Example 6 was repeated except that (1) the organophosphorus compound component of the catalyst system was triphenylphosphine (0.1 g), (2) the process solvent was 2-octanone (50 mL), and (3) the hydrogenation was carried out over a period of 2 hours. The results obtained are shown in Table I.

EXAMPLE 38

Example 6 was repeated except that (1) the organophosphorus compound component of the catalyst system was dioctylphenylphosphine (0.1 g), (2) the process solvent was dimethyl phthalate (50 mL), and (3) the hydrogenation was carried out over a period of 2 hours. The results obtained are shown in Table I.

EXAMPLE 39

Example 6 was repeated except that the process solvent was cyclohexanone (50 mL). The results obtained are shown in Table I.

EXAMPLE 40

Example 6 was repeated except that the process solvent was butanone (50 mL). The results obtained are shown in Table I.

EXAMPLE 41

Example 6 was repeated except that the process solvent was n-propanol (50 mL). The results obtained are shown in Table I.

EXAMPLE 42

Example 6 was repeated except that (1) the organophosphorus component of the catalyst system was 1,2-bis(diphenyl)ethane (0.1 g) and (2) the hydrogenation was carried out over a period of 2 hours. The results obtained are shown in Table I.

EXAMPLE 43

Example 6 was repeated except that the organophosphorus component of the catalyst system was triphenyl phosphite (0.1 g). The results obtained are shown in Table I.

EXAMPLE 44

Example 6 was repeated except that the organophosphorus component of the catalyst system was 2,2'-bis(diphenylphosphinomethyl)- 1,1'-biphenyl (0.1 g). The results obtained are shown in Table I.

EXAMPLE 45

Example 6 was repeated except that (1) the organophosphorus component of the catalyst system was trioctylphosphine (0.1 g) and (2) the hydrogenation was carried out over a period of 2 hours. The results obtained are shown in Table I.

EXAMPLE 46

Example 6 was repeated except that (1) the organophosphorus component of the catalyst system was α,α'-bis(diphenylphosphino)-o-xylene (0.1 g) and (2) the hydrogenation was carried out over a period of 2 hours. The results obtained are shown in Table I.

EXAMPLE 47

Example 6 was repeated except that (1) the organophosphorus component of the catalyst system was 1,4-bis-(diphenylphosphino)butane (0.1 g) and (2) the hydrogenation was carried out over a period of 2 hours. The results obtained are shown in Table I.

EXAMPLE 48

Example 6 was repeated except that (1) the organophosphorus component of the catalyst system was 1,6-bis-(diphenylphosphino)hexane (0.1 g) and (2) the hydrogenation was carried out over a period of 2 hours. The results obtained are shown in Table I.

EXAMPLE 49

Example 6 was repeated except that the organophosphorus component of the catalyst system was 1-diphenylphosphino- 2-(2-pyridyl)ethane (0.1 g). The results obtained are shown in Table I.

TABLE I

| Example | EpB Conv | BO % | HBu % | BuOH % |
|---|---|---|---|---|
| 1 | 97.9 | 88.7 | 5.1 | 6.2 |
| 2 | 96.3 | 80.2 | 8.2 | 11.6 |
| 3 | 91.8 | 83.8 | 7.0 | 9.2 |
| 4 | 100 | 89.9 | 4.2 | 5.9 |
| 5 | 100 | 90.5 | 2.2 | 5.9 |
| 6 | 99.1 | 88.1 | 4.7 | 7.2 |
| 7 | 98.9 | 88.5 | 6.9 | 4.6 |
| 8 | 99.9 | 90.3 | 0.8 | 9.0 |
| 9 | 81.3 | 93.9 | 3.3 | 2.8 |
| 10 | 96.3 | 95.9 | 3.1 | 1.0 |
| 11 | 91.1 | 95.5 | 3.7 | 0.7 |
| 12 | 100 | 80.6 | 3.9 | 15.5 |
| 13 | 100 | 80.1 | 1.0 | 18.9 |
| 14 | 100 | 84.1 | 6.8 | 9.1 |
| 15 | 97.4 | 82.1 | 8.0 | 9.8 |
| 16 | 97.7 | 77.2 | 10.2 | 12.8 |
| 17 | 100 | 76.6 | 2.9 | 15.8 |
| 18 | 100 | 86.7 | 3.7 | 9.6 |
| 19 | 100 | 86.2 | 5.5 | 8.3 |
| 20 | 81.3 | 81.8 | 5.2 | 13.0 |
| 21 | 95.5 | 74.4 | 12.0 | 13.5 |
| 22 | 100 | 88.4 | 0.8 | 10.8 |
| 23 | 99.5 | 84.0 | 9.0 | 7.0 |
| 24 | 45.4 | 91.6 | 3.5 | 4.9 |
| 25 | 91.0 | 90.2 | 4.0 | 5.7 |
| 26 | 100 | 70.4 | 10.5 | 19.1 |
| 27 | 100 | 88.4 | 0.8 | 10.8 |
| 28 | 100 | 85.0 | 5.2 | 9.8 |
| 29 | 100 | 70.4 | 19.3 | 10.3 |
| 30 | 98.3 | 70.8 | 14.6 | 14.6 |
| 31 | 53.8 | 79.7 | 15.8 | 4.6 |
| 32 | 91.7 | 82.5 | 11.2 | 6.3 |
| 33 | 98.8 | 80.3 | 7.3 | 12.4 |
| 34 | 100 | 53.8 | 24.4 | 21.7 |
| 35 | 100 | 58.9 | 10.6 | 30.5 |
| 36 | 100 | 70.2 | 15.2 | 14.6 |
| 37 | 100 | 79.0 | 5.8 | 15.2 |
| 38 | 97.1 | 74.4 | 8.8 | 16.8 |
| 39 | 100 | 90.8 | 4.8 | 4.4 |
| 40 | 100 | 66.2 | 9.5 | 24.4 |
| 41 | 100 | 69.5 | 6.2 | 24.3 |
| 42 | 45.1 | 89.7 | 3.5 | 6.8 |
| 43 | 51.9 | 89.0 | 6.1 | 4.9 |
| 44 | 100 | 54.1 | 13.8 | 32.2 |
| 45 | 99.6 | 80.9 | 8.2 | 10.9 |
| 46 | 100 | 72.3 | 11.4 | 16.3 |
| 47 | 100 | 70.1 | 13.4 | 16.6 |
| 48 | 99.5 | 57.3 | 12.9 | 29.9 |
| 49 | 70.4 | 78.2 | 11.7 | 10.1 |

EXAMPLE 50

Example 6 was repeated except that the epoxyalkene reactant was 1,2-epoxy-5-hexene (10 mL). Analyses of the product reaction mixture showed that all of the 1,2-epoxy-5-hexene had been converted to 1,2-epoxy-hexane.

EXAMPLE 51

Example 6 was repeated except that (1) the epoxyalkene reactant was 1,2-epoxy-7-octene (5 mL) and (2) the process solvent was acetone (50 mL). Analyses of the product reaction mixture showed that 84.8% of the 1,2-epoxy-7-octene had reacted with 100% selectivity to 1,2-epoxyoctane.

EXAMPLE 52

Example 6 was repeated except that the epoxyalkene reactant was allyl glycidyl ether (10 mL). Analyses of the product reaction mixture showed 100% conversion of the allyl glycidyl ether reactant with greater than 95% selectivity to the desired propyl glycidyl ether product.

The invention has been described in detail with particular reference to preferred embodiments thereof, but it will be understood that variations and modifications may be effected within the spirit and scope of the invention.

I claim:

1. A catalyst solution comprising (A) an inert, organic solvent and (B) catalyst components dissolved in said solvent comprising (i) rhodium, (ii) an organophosphorus compound selected from trihydrocarbylphosphines and trihydrocarbylphosphites, and (iii) a poly-unsat-urated hydrocarbon selected from alkadienes, cycloalkadienes, alkatrienes and cycloalkatrienes;

wherein the ratio of moles of component (ii) to gram atoms of rhodium is about 3:1 to 50:1; and the ratio of moles of component (iii) to gram atoms of rhodium is about 2:1 to 150:1.

2. A catalyst solution according to claim 1 comprising (A) an inert, organic solvent containing up to about 12 carbon atoms and (B) catalyst components dissolved in said solvent comprising (i) rhodium, (ii) a trihydrocarbylphosphine, (iii) a poly-unsaturated hydrocarbon selected from alkadienes and cycloalkadienes containing 4 to 10 carbon atoms, and (iv) a non-nucleophilic gegen ion;

wherein the ratio of moles of component (ii) to gram atoms of rhodium is about 3:1 to 50:1;

the ratio of moles of component (iii) to gram atoms of rhodium is about 2:1 to 150:1.

3. A catalyst solution according to claim 2 wherein the organic solvent is a ketone having 3 to 8 carbon atoms.

4. A catalyst solution comprising (A) an inert, organic solvent selected from ketones containing from 3 to 8 carbon atoms and (B) catalyst components dissolved in said solvent comprising (i) rhodium, (ii) a trihydro-carbylphosphine wherein each hydrocarbyl group contains up to about 12 carbon atoms, (iii) a poly-unsaturated hydrocarbon selected from alkadienes and cycloalkadienes containing 4 to 10 carbon atoms, and (iv) a non-nucleophilic gegen ion;

wherein the ratio of moles of component (ii) to gram atoms of rhodium is about 4:1 to 20:1; and the ratio of moles of component (iii) to gram atoms of rhodium is about 5:1 to 10:1.

5. A catalyst solution according to claim 4 wherein (i) the concentration of rhodium in the catalyst solution is in the range of 100 to 2000 ppm, (ii) the trihydrocarbylphosphine is selected from triphenyl-phosphine, tricyclohexylphosphine and tribenzylphosphine, and (iii) the non-nucleophilic gegen ion is selected from hexafluorophosphate and boron compounds having the formula $(R^5)_4B^- M^+$ wherein $R^5$ is selected from fluorine, hydrogen, alkyl, aryl, or hetero aryl, and M is an alkali metal.

6. A catalyst solution comprising (A) an inert, organic solvent selected from ketones containing from 3 to 8 carbon atoms and (B) catalyst components dissolved in said solvent comprising (i) rhodium, (ii) a trihydrocarbylphosphine wherein each hydrocarbyl group contains up to about 12 carbon atoms, (iii) a polyunsaturated hydrocarbon selected from alkadienes and cycloalkadienes containing 4 to 10 carbon atoms, (iv) a non-nucleophilic gegen ion, and (v) iodide;
wherein
    the ratio of moles of component (ii) to gram atoms of rhodium is about 4:1 to 20:1;
    the ratio of moles of component (iii) to gram atoms of rhodium is about 5:1 to 10:1 and
    the ratio of gram atoms of iodide per gram atom of rhodium is about 0.25 to 5.0.

7. A catalyst solution according to claim 6 wherein (i) the concentration of rhodium in the catalyst solution is in the range of 100 to 2000 ppm, (ii) the trihydrocarbylphosphine is selected from triphenylphosphine, tricyclohexylphosphine and tribenzylphosphine, and (iii) the non-nucleophilic gegen ion is selected from hexafluorophosphate and boron compounds having the formula $(R^5)_4B^-M^+$ wherein $R^5$ is selected from fluorine, hydrogen, alkyl, aryl, or hetero aryl, and M is an alkali metal.

* * * * *